(12) United States Patent
Min et al.

(10) Patent No.: US 7,321,792 B1
(45) Date of Patent: Jan. 22, 2008

(54) PACING THERAPY AND ACUPUNCTURE

(75) Inventors: Xiaoyi Min, Thousand Oaks, CA (US); Gene A. Bornzin, Simi Valley, CA (US); Mark W. Kroll, Simi Valley, CA (US); Xing Pei, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 567 days.

(21) Appl. No.: 10/392,619

(22) Filed: Mar. 19, 2003

(51) Int. Cl.
*A61N 1/08* (2006.01)
*A61N 1/36* (2006.01)

(52) U.S. Cl. .......................... 607/3; 128/907
(58) Field of Classification Search ................ 607/59, 607/61, 1–3; 600/16, 17; 128/907
See application file for complete search history.

(56) References Cited

U.S. PATENT DOCUMENTS

| | | | |
|---|---|---|---|
| 4,712,555 A | 12/1987 | Thornander et al. ........ 128/419 |
| 4,788,980 A | 12/1988 | Mann et al. ................. 128/419 |
| 4,940,052 A | 7/1990 | Mann et al. ................. 128/419 |
| 4,944,298 A | 7/1990 | Sholder ....................... 128/419 |
| 5,466,254 A | 11/1995 | Helland ....................... 607/123 |
| 5,476,483 A | 12/1995 | Bornzin et al. ............... 607/17 |
| 5,522,854 A | 6/1996 | Ideker et al. .................. 607/6 |
| 5,662,689 A * | 9/1997 | Elsberry et al. ............... 607/5 |
| 5,782,882 A | 7/1998 | Lerman et al. |
| 5,792,187 A | 8/1998 | Adams ........................... 607/5 |
| 5,817,131 A | 10/1998 | Elsberry et al. ................ 607/5 |
| 5,836,971 A | 11/1998 | Starkweather |
| 5,893,881 A | 4/1999 | Elsberry et al. ................ 607/5 |
| 6,058,328 A | 5/2000 | Levine et al. |
| 6,154,672 A | 11/2000 | Pendekanti et al. |
| 6,314,323 B1 | 11/2001 | Ekwall ........................ 607/23 |
| 6,349,233 B1 | 2/2002 | Adams ......................... 607/5 |
| 6,377,853 B1 | 4/2002 | Malaney et al. ............... 607/61 |
| 6,522,926 B1 * | 2/2003 | Kieval et al. ................. 607/44 |
| 6,650,936 B2 | 11/2003 | Sullivan et al. |
| 6,662,051 B1 * | 12/2003 | Eraker et al. ................. 607/59 |
| 6,832,982 B1 * | 12/2004 | Lapanashvili et al. ........ 600/16 |

OTHER PUBLICATIONS

Crevenna et al., "Electromagnetic Interference by Transcutaneous Neuromuscular Electrical Stimulation in Patients with Bipolar Sensing Implantable Cardioverter Defibrillators: A Pilot Safety Study," Pacing Clin Electrophysiol., Feb. 2003; 26 (2 Part 1): 626-629.
Pyatt et al., "The Simultaneous Use of a Biventricular Implantable Cardioverter Defribillator (ICD) and Transcutaneous Electrical Nerve Stimulation (TENS) Unit: Implications for Device Interaction," Europace, Jan. 2003; 5:91-93.
Cho et al., "New Findings of the Correlation Between Acupoints and Corresponding Brain Cortices Using Functional MRI," Proc. Natl. Acac. Sci. USA, 1998; 95(5):2670-2673.

(Continued)

*Primary Examiner*—George R. Evanisko
*Assistant Examiner*—Michael Kahelin

(57) ABSTRACT

Exemplary methods, devices and/or systems for detecting one or more needs and for requesting the delivery of power to one or more acupoints. Other methods, devices and/or systems are also disclosed.

13 Claims, 14 Drawing Sheets

OTHER PUBLICATIONS

Wu et al., "Central Nervous Pathway for Acupuncture Stimulation: Localization of Processing with Functional MR Imaging of the Brain—Preliminary Experience," Radiology 1999; 212:133-141.

Chao et al., "Naloxone Reverses Inhibitory Effect of Electroacupuncture of Sympathetic Cardiovascular Reflex Response", Amer. Physi. Society 1999; 276(6):H2127-H2134.

Knardahl et al., "Sympathetic Nerve Activity After Acupuncture in Humans", Pain 1998; 75:19-25.

Siedentopf et al., "Functional Magnetic Resonance Imaging Detects Activation of the Visual Association Cortex During Laser Acupuncture of the Foot in Humans", Neuroscience Letters 2002; 327:53-56.

Hsieh et al., "Activation of the Hypothalamus Characterizes the Acupuncture Stimulation at the Analgesic Point in Human: a Positron Emission Tomography Study," Neuroscience Letters, 2001; 307:105-108.

Yun-Hui et al., "Tinggong(SI19), A Novel Acupoint for 2Hz Electroacupuncture-induced Depressor Response," Acup. & Elec.-Therap. Res., Inc. J., 1993; 18:89-96.

Yang et al., "Effect of Electroacupuncture on Response to Immobilization Stress," Pharm. Biochem. And Behavior, 2002; 72:847-855.

Nishijo et al., "Decreased Heart Rate by Acupuncture Stimulation in Humans via Faciliation of Cardiac Vagal Activity and Suppression of Cardiac Sympathetic Nerve," Neuroscience Letters, 1997: 227:165-168.

Syuu et al., "Cardiovascular Beneficial Effects of Electroacupuncture at Neiguan (PC-6) Acupoint in Anesthetized Open-Chest Dog," Japanese Jour. Of Physio., 2001; 51:231-238.

Li et al., "Rostral Ventrolateral Medullary Opioid Receptor Subtypes in the Inhibitory Effect of Electroacupuncture on Reflex Autonomic Response in Cats," Autonomic Neurosc.: Basic & Clinical, 2001; 89:38-47.

Baklavadzhyan et al., "Studies of the Role of the Central Nucleus of the Amygdala in Controlling Cardiovascular Functions," Neuros. & Behav. Physio., 2000: 30(2):231-236.

Zhongfang et al., "Role of Amygdaloid Nucleus in the Correlation Between the Heart and the Acupoint Neiguan in Rabbits," Jour. Of Trad. Chinese Med., 1991; 11(2):128-138.

Ku et al., "Beta-Endorphin-and GABA-Mediated Depressor Effect of Specific Electroacupuncture Surpasses Pressor Response of Emotional Circuit," Peptides, 2001; 22:1465-1470.

Hui et al., "Acupuncture Modulates the Limbic System and Subcortical Gray Structures of the Human Brain: Evidence From fMRI Studies in Normal Subjects," Human Brain Mapping, 2000; 9:13-25.

Nalivaiko et al., "Raphe Region Mediates Changes in Cutaneous Vascular Tone Elicited by Stimulation of Amygdala and Hypothalamus in Rabbits," Brain Research, 2001; 891:130-137.

Wang et al., "Effect of the Intensity of Transcutaneous Acupoint Electrical Stimulation of the Postoperative Analgesic Requirement," Anesth. Analg., 1997; 85:406-413.

Chen, "Acupuncture and Herbs in the Treatment of Neurodegenerative Disorders: Alzheimer's Disease, Stroke, and Parkinson's Disease," Med. Acupun., 1999; 11(1).

Xian et al., "Effect of Acupuncture on Heart Rate Variability in Coronary Heart Disease Patients," Zhongguo Zhong Xi Yi Jie He Za Zhi, 1995; 15(9):536-538.

Fujiwara et al., "The Influence of Low Frequency Acupuncture on a Demand Pacemaker," Chest, 1980; 78(1):96-97.

Li et al., "Reversal of Reflex-Induced Myocardial Ischemia by Median Nerve Stimulation, A Feline Model of Electroacupuncture," Circulation, 1998; 97:1186-1194.

Smith, "Acupuncture for Cardiovascular Disorders," Prob. In Vet. Med., 1992; 4(1):125-131.

Balogun et al., "The Effects of Acupuncture, Electroneeding and Transcutaneous Electrical Stimulation Therapies on Pheripheral Haemodynamic Functioning," Disab. & Rehab., 1998; 20(2):41-48.

Shen, "Research on the Neurophysiological Mechanisms of Acupuncture: Review of Selected Studies and Methodological Issues," Journ.of Alt. & Comle. Med., 2001; 7(1):S-121-S-127.

Lin et al., "Low and High Frequency Electroacupuncture at Hoku Elicits a Distinct Mechanism to Activate Sympathetic Nervous System in Anesthetized Rats," Neuro. Letters, 1998; 247:155-158.

Xia et al., "Inhibitory Effect of * Analogous Electro-Acupuncture on Experimental Arrythmia," Acup. & Elec.-Therp. Res., Int. J., 1985; 10:13-34.

Hoffmann et al., "Long-Lasting Cardiovascular Depression Induced by Acupuncture-Like Stimulation of the Sciatic Nerve in Unanaesthetized Rats. Effects of Arousal and Type of Hypertension," Acta Physio. Scand., 1986; 127:119-126.

Jacobsson et al., "The Effect of Transcutaneous Electric Nerve Stimulation in Patients with Therapy-Resistant Hypertension," Journ. Of Human Hyper., 2000; 14:795-798.

Haker et al., "Effect of Sensory Stimulation (Acupuncture) on Sympathetic and Parasympathetic Activities in Healthy Subjects," Journ. of the Auton. Nervous Sys., 2000; 79:52-59.

Abad-Alegria et al., "Objective Assessment of the Sympatholytic Action of the Nei-Kuan Acupoint," Amer. Journ. of Chinese Med., 2001; 29(2):201-210.

Shinohara, "Decreasing Heart Rate and Shortening of the Arterial Pulse Propagation Time by Acupuncture in the Spectral Analyses," Masui, 1997; 46(2):213-221.

Kostov et al., "Influence of Laser Acupuncture and Radiation of the Cervix of the Uterus in Cows on the Cardiac Activity and Morphologic Composition of Blood," Vet. Med. Nauki, 1987; 24(10):36-43.

Faure-Antonietti et al., "Traitement Using Traditional Acupuncture of Early Scapulohumeral Pains Following Heart Surgery," Cah Anesthesiol, 1991; 39(8):537-540.

Zhili et al., "The Segmental Distribution of Sympathetic Afferent Neurons of the Heart Cardiac Nerve, and Projection of the Cardiac Nerve to the Central Nervous System," Zhen Ci Yan Jiu, 1993: 18(4):257-261.

Ballegaard et al., "Addition of Acupuncture and Self-Care Education in the Treatment of Patients with Severe Angina Pectoris May be Cost Beneficial: An Open, Prospective Study," Journ. of Alt. & Comp. Med., 1999; 5(5):405-413.

* cited by examiner

EXEMPLARY SLAVE DEVICE

EXEMPLARY METHOD

PACING THERAPY AND ACUPUNCTURE

TECHNICAL FIELD

Exemplary methods and/or devices presented herein generally relate to cardiac pacing and/or stimulation therapy. Various exemplary methods and/or devices concern stimulation of acupuncture points.

BACKGROUND

Various therapies, known to or stemming from traditional Oriental medicine, rely on pressure, needle, electric and/or magnetic stimulation of specific points in the human body. Many of these therapies emphasize energy balancing; consider Chinese acupuncture (Zhen Jiu) which aims to balance a vital energy known as Qi. According to traditional acupuncture, Qi interacts with vital substances such as Xue (blood), Jing (essence), Shen (spirit), and Jin Ye (bodily fluids). For example, Xue follows Qi through the body primarily via twelve main energy ducts called meridians wherein each of these meridians connects to one of twelve organs. Acupuncture models typically show meridians as lines running and occasionally crossing throughout the body wherein individual acupuncture points, or acupoints, fall along the meridians. According to the practice of acupuncture, acupoint stimulation can release blockages, balance Qi and restore the body to its natural state. A practitioner of acupuncture typically stimulates an acupoint through manual manipulation of a fine needle inserted subcutaneously at an acupoint; whereas, a practioner of acupressure (Zhi Ya) may apply pressure to stimulate an acupoint. More recently however, electric and/or magnetic energy have been used to stimulate acupoints, for example, consider electroacupuncture which has generally proven to be more convenient and effective than manual stimulation.

While Western medicine has typically viewed acupuncture relatively simply (e.g., as synonymous with nerve stimulation), recent studies support the Oriental view that meridians and acupoints have special significance. In particular, various studies suggest that acupoint stimulation produces a result essentially different than that of non-acupoint stimulation. To elucidate such differences, researchers have begun using functional magnetic resonance imaging (fMRI) or positron emission tomography (PET) to map brain activity responsive to stimulation at acupoints and non-acupoints. A study by Cho et al., "New findings of the correlation between acupoints and corresponding brain cortices using functional MRI," *Proc. Natl. Acac. Sci.* USA, 95(5):2670-2673 (1998), showed that ancient acupuncture literature correctly associated acupoints with particular organs or brain activity. More specifically, Cho, et al., demonstrated that stimulation at acupoint BL.67 (Zhi Yin), located on the foot and known for treatment of eye disorders, activated the occipital lobes whereas stimulation of non-acupoints (e.g., points displaced by 2 cm to 5 cm) did not activate the occipital lobes. A later study by Siedentopf, et al., "Functional magnetic resonance imaging detects activation of the visual association cortex during laser acupuncture of the foot in humans," *Neurosci. Lett.*, 327(1):53-56 (2002), confirmed that acupoint stimulation at BL.67 activated the visual cortex. These studies lend credence to a wealth of traditional therapies based on acupoint stimulation.

Another study, by Wu et al., "Central nervous system pathway for acupuncture stimulation: localization of processing with functional MR imaging of the brain—preliminary experience," *Radiology*, 212:133-141 (1999), examined acupuncture at two acupoints, well-known for analgesia, and "minimal" acupuncture at non-acupoints (e.g., points displaced by 2 cm to 3 cm). Wu, et al., reported that acupuncture at LI.4 (Hegu) and ST.36 (Zusanli) produced bradycardia and activation of the hypothalamus and nucleus accumbens and deactivation of the rostral part of the anterior cingulated cortex, amygdala formation, and hippocampal complex; whereas, minimal acupuncture at the non-acupoints produced activation of the supplementary motor cortex, parietal operculum, and frontal operculum. Wu et al. also detected a more extensive activation of the hypothalamus for stimulation of the LI.4 acupoint compared to the ST.36 acupoint and noted that this result coincides with clinical observations that show stimulation at LI.4 produces a stronger analgesic effect than stimulation at ST.36. On the basis of their results, Wu, et al., hypothesized that bradycardia is characteristic of an acupuncture-related autonomic response and that acupuncture analgesia is associated with deactivation of limbic areas and attenuation of the affective response to pain. Wu, et al., also recognized that acupuncture often has analgesic and non-analgesic effects. A later study by Hsieh et al., "Activation of the hypothalamus characterizes the acupuncture stimulation at the analgesic point in human: a positron emission tomography study," *Neurosci. Lett.*, 307(2):105-108 (2001), also examined stimulation at the LI.4 acupoint and a non-acupoint. Hsieh et al. found that stimulation of the LI.4 acupoint activated the hypothalamus while stimulation of the non-acupoint did not. These studies support the traditional practice of acupoint stimulation for treatment of pain as well as other disorders.

Overall, studies using modern imaging modalities have effectively proven that acupoint stimulation can produce therapeutic action. In the realm of cardiac pacing and/or stimulation therapies, acupoint stimulation holds promise. However, as reported by Fujiwara et al., "The influence of low frequency acupuncture on a demand pacemaker," *Chest*, 78:96-97 (1980), found that low frequency acupuncture caused electromagnetic interference capable of interfering with demand sensing. Indeed, electroacupuncture is often contraindicated for patients having implanted pacing and/or stimulation devices, especially devices that rely on sensing. Therefore, a need exists for methods, devices and/or systems that allow cardiac pacing and/or stimulation therapy patients to benefit from electric and/or magnetic acupoint stimulation therapy. Various methods, devices and/or systems that address this need and/or other needs are described below.

SUMMARY

Exemplary methods, devices and/or systems are provided for detecting one or more needs and for requesting the delivery of power to one or more acupoints. For example, an implantable cardiac therapy device may detect a need for anti-arrhythmia therapy and communicate the need to a slave device, which, in turn, delivers power to an acupoint that may have an analgesic, anti-arrhythmic, and/or other beneficial effect. Alternatively, the slave device notifies a patient (or other individual) to administer a potentially beneficial acupuncture therapy. Other methods, devices and/or systems are also disclosed.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices and/or systems described herein are suitable for use with electroacupuncture and/or suitable for delivering cardiac therapy (e.g., sensing, detecting, pacing and/or stimulation therapy) in combination with electroacupuncture. For example, an exemplary implantable cardiac device (e.g., an ICD, etc.) includes filtering, blanking and/or other features to minimize electromagnetic interference associated with electroacupuncture or even transcutaneous nerve stimulation. Such a device optionally allows for use of an electromagnetically transmitted code to notify the device of an impending electroacupuncture session. In response thereto, the exemplary device takes appropriate action to ensure that the electroacupuncture session does not interfere with cardiac pacing or stimulation therapy. Another exemplary implantable cardiac device (e.g., an ICD, etc.) includes circuitry and logic capable of delivering power to one or more acupoints and/or requesting delivery of power to one or more acupoints. For example, a device capable of delivering a cardioversion stimulus, may include circuitry and logic for delivering power to one or more acupoints to produce an analgesic effect in an effort to minimize pain associated with a cardioversion stimulus. Yet another exemplary implantable cardiac device (e.g., an ICD, etc.) includes circuitry and logic capable of delivering power to one or more acupoints for treatment of angina, arrhythmia and/or other disorders.

Described below are at least exemplary implantable devices, exemplary slave devices, exemplary acupoints suitable for stimulation, and exemplary methods of using various exemplary implantable devices and/or various exemplary slave devices in combination with electroacupuncture.

Exemplary Stimulation Device

Various exemplary methods described below are optionally implemented in connection with a stimulation device such as the exemplary stimulation device 100 of FIG. 1.

Figure 1:
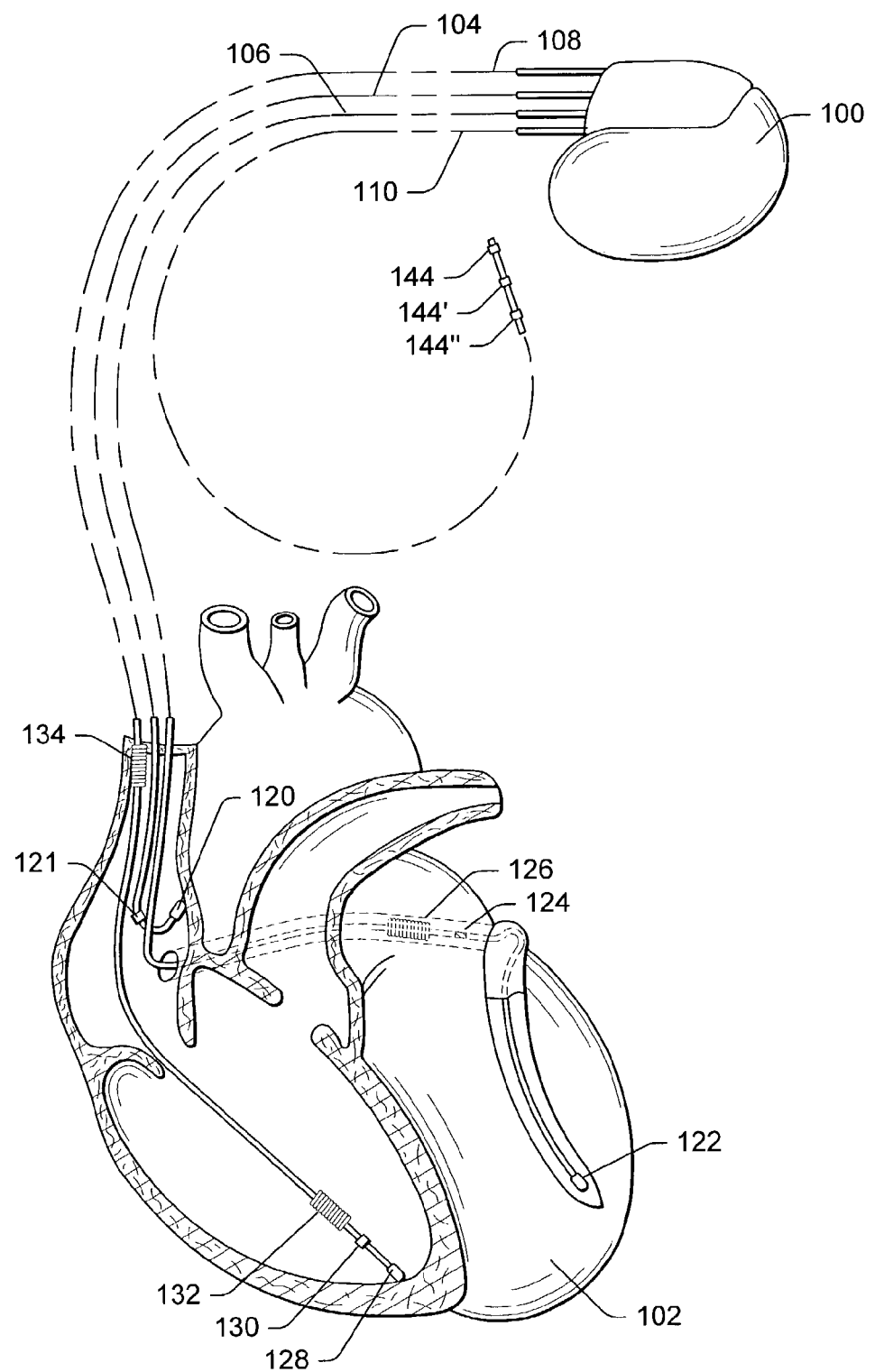
FIG. 1 is a simplified diagram illustrating an exemplary implantable stimulation device (e.g., an ICD, etc.) in electrical communication with at least three leads implanted into a patient's heart and at least one other lead for delivering stimulation and/or shock therapy.

FIG. 1 shows the exemplary stimulation device 100 in electrical communication with a patient's heart 102 by way of three leads 104, 106, 108, suitable for delivering multichamber stimulation and shock therapy. The leads 104, 106, 108 are optionally configurable for delivery of stimulation pulses suitable for stimulation at acupuncture points (e.g., acupoints on meridians, etc.). In addition, the device 100 includes a fourth lead 110 having, in this implementation, three electrodes 144, 144', 144" suitable for stimulation at acupoints. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation at one or more acupoints.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
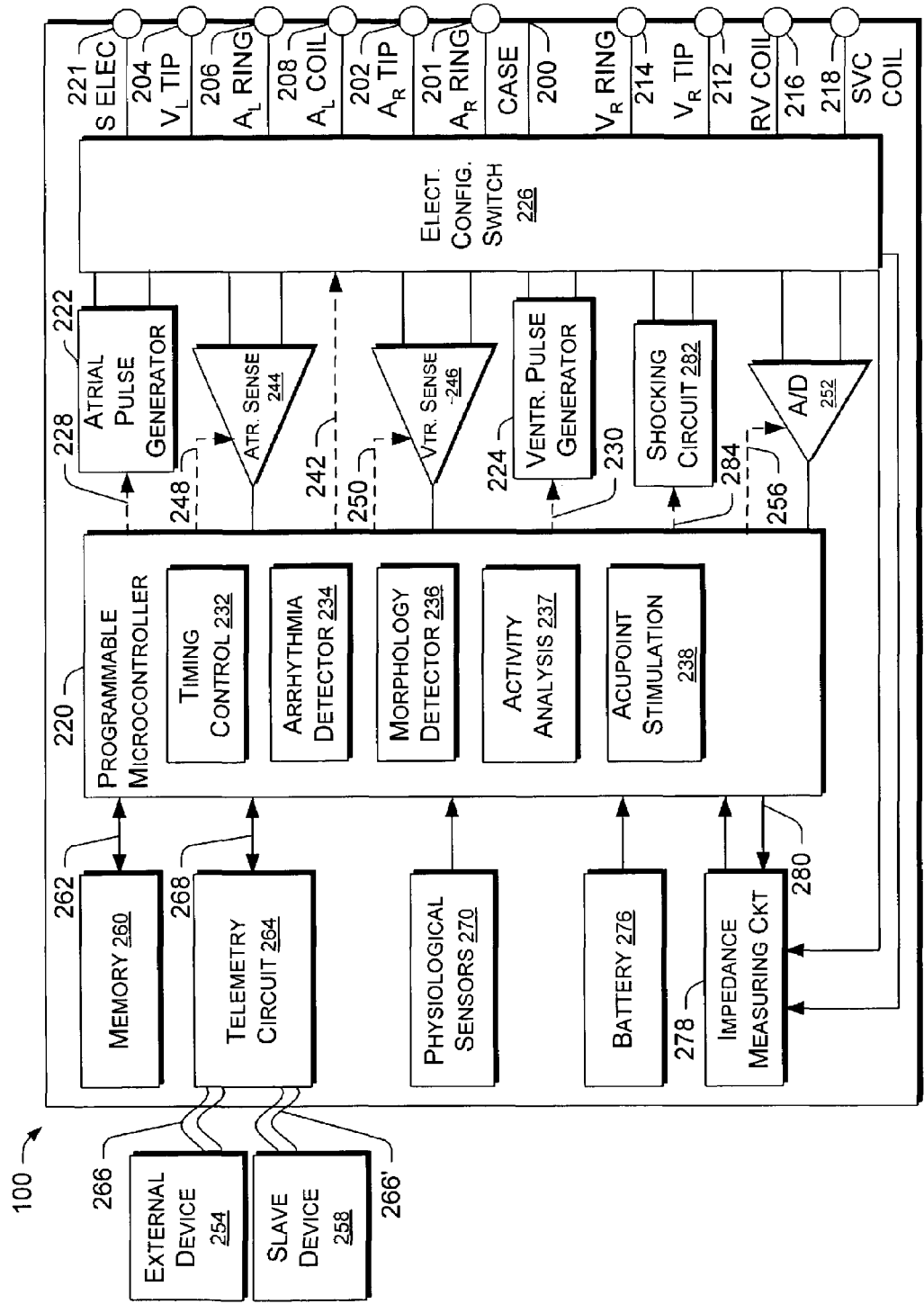
FIG. 2 is a functional block diagram of an exemplary implantable stimulation device (e.g., an ICD, etc.) illustrating basic elements that are configured to provide cardioversion, defibrillation, pacing stimulation, autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to one or more accupoints) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity. For example, the atrial activity analysis module 237 optionally implements one or more of the exemplary methods described below.

Microcontroller 220 further includes an acupoint stimulation module 238 for performing a variety of tasks related to acupoint stimulation, including blanking, filtering, etc. of signals related to acupoint stimulation. This component can be utilized by the stimulation device 100 for determining desirable times to administer various therapies. The acupoint module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest.

Further, such filtering is optionally pre-programmed, preselected and/or programmable to address interference stemming from acupoint stimulation. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The telemetry circuit 264 is optionally in telemetric communication via the communication link 266' with a slave device 258. The slave device 258 may be internal (i.e., at least partially implanted in a patient) or external. As described in more detail below, various slave devices have an ability to deliver a stimulus to an acupoint (or other point) while other slave devices signal a user to administer acupuncture therapy and/or other therapy. Communication between the exemplary device 100 and the slave device 258 may occur in bidirectional and/or unidirectional manner.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 optionally measures impedance at or near an acupoint. For example, an electrode may have impedance that varies with its position in relation to an acupoint. Thus, the impedance measuring circuit 278 may detect when an electrode is properly or improperly positioned with respect to an acupoint. Such a circuit may aid in the positioning of an electrode for electroacupuncture therapy. Further, such a circuit may be used to locate a point having known impedance.

In the description herein, the term ICD typically refers to an implantable cardiac device, for example, an implantable device capable of cardiac therapy (e.g., sensing, detecting, pacing, and/or stimulation therapies, etc.). Various exemplary methods and/or exemplary systems optionally rely on an implantable device, which may be an ICD. In general, the stimulation device 100 is an ICD. The term ICD includes also includes implantable cardioverter/defibrillator device. In the case where the stimulation device 100 is intended to operate as an implantable cardioverter/defibrillator device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Exemplary Implantable Cardiac Device and Acupoint Stimulator

Figure 3:
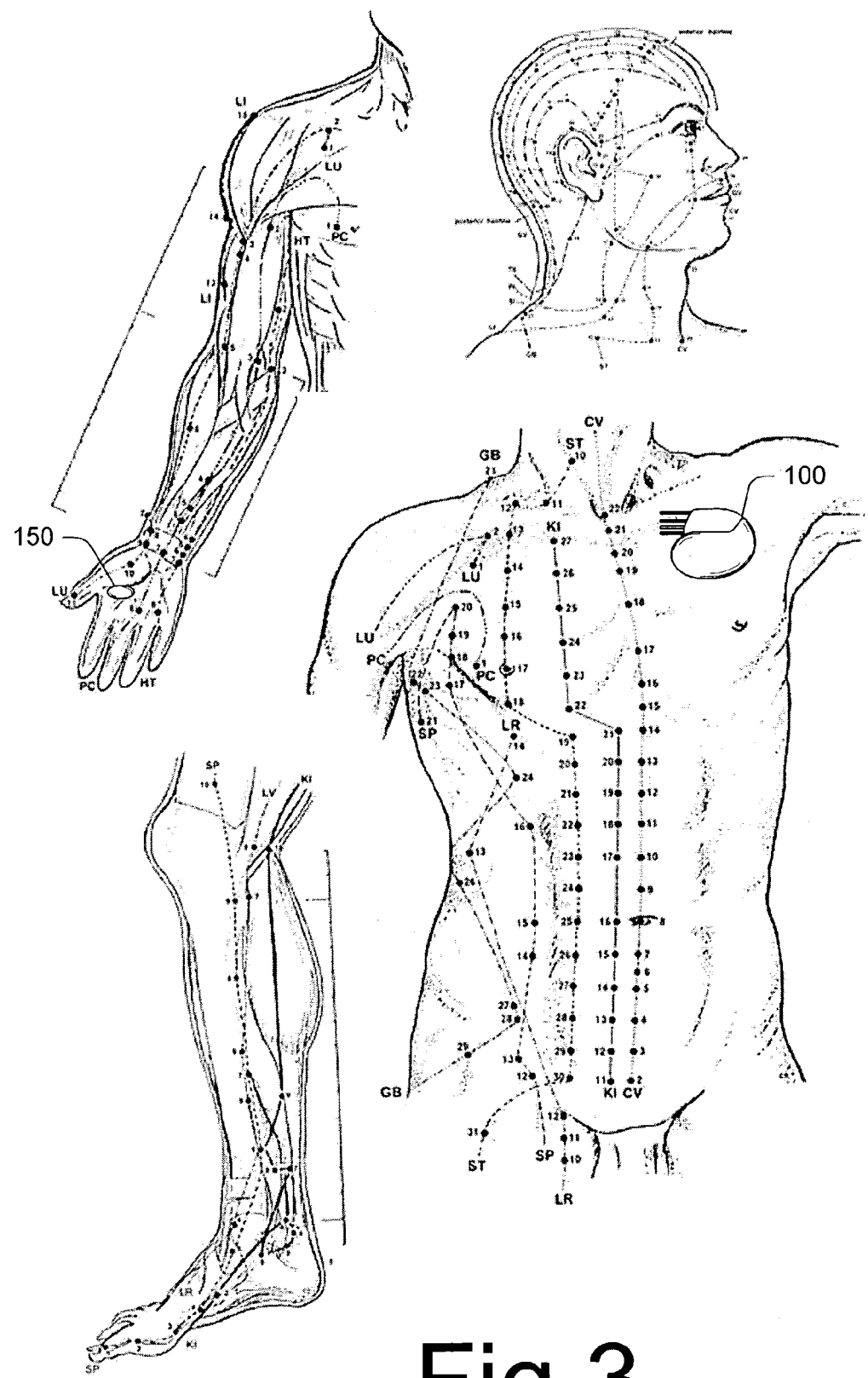
FIG. 3 is an approximate anatomical diagram including an implantable cardiac device (ICD) and a slave device.

Referring to FIG. 3, an exemplary ICD 100 (e.g., the stimulation device 100 of FIG. 1, etc.) and an acupoint stimulator 150 are shown along with various diagrams of the human body. In this example, the ICD 100 is implanted in a patient's chest and the acupoint stimulator 150 is positioned at the patient's hand (e.g., at or near an acupoint). The acupoint stimulator 150 optionally operates independent of the ICD 100 or operates in a manner that depends on the ICD 100. In the latter instance, the acupoint stimulator 150 may simply include one or more electrodes on a lead connected to the ICD 100. In general, the acupoint stimulator 150 is not limited in size and it is positionable at or near an acupoint and capable of stimulation at or near the acupoint. Further, the acupoint stimulator 150 may operate as a slave device (see, e.g., the slave device 258 of FIG. 2). As a slave device, the acupoint stimulator 150 may receive telemetric commands communicated from the ICD 100. The acupoint stimulator 150 may alternatively, or in addition to, communicate information to the ICD 100. Thus, the exemplary acupoint stimulator 150 may communicate in a unidirectional or bidirectional manner with the exemplary ICD 100. Yet further, as already mentioned, an ICD may communicate with a slave device that simply notifies a patient to administer acupuncture therapy or suitable other therapy.

Figure 4:
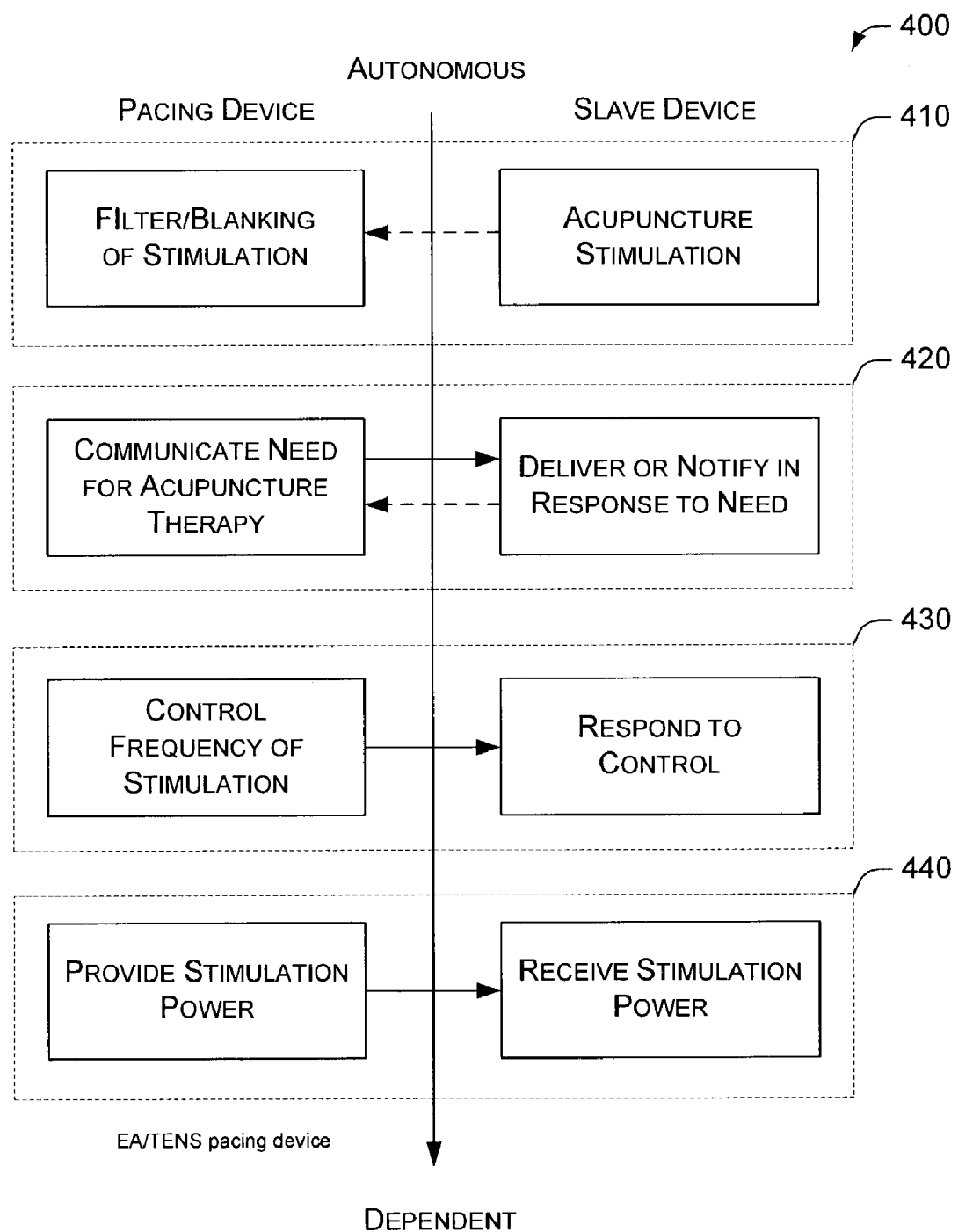
FIG. 4 is an exemplary spectrum showing exemplary relationships between an implantable cardiac device (ICD) and a slave device.

Referring to FIG. 4, an exemplary spectrum 400 ranging from autonomous to dependent is shown to describe possible relationships between an ICD and a slave device (e.g., notification device, acupoint stimulator, etc.). In a first scenario 410, an ICD includes appropriate circuitry to operate properly regardless of electromagnetic interference generated by electroacupuncture, transcutaneous electrical nerve stimulation (TENS), etc while a slave device (e.g., an electroacupuncture stimulator, TENS stimulator, etc.) operates independent of the ICD. In this scenario, the slave device optionally transmits a code to the ICD to notify the ICD of an impending stimulation session. Alternatively, the ICD may sense such stimulation and respond appropriately, for example, based on magnitude and frequency of the applied stimulation. In this alternative, the ICD only requires an ability to recognize such stimulation; thus, the slave device and ICD are quite independent.

In a second scenario 420, an ICD detects a need for acupuncture or related therapy and communicates the need. For example, an ICD may detect a need for acupuncture or related therapy and then communicate information about the need to a slave device. In response, the slave device may delivery and/or notify in response to the communicated information. In general, the information calls for administration of acupuncture or related therapy. For example, where the slave device is capable of administering such therapy, the slave device would receive the communicated information and respond accordingly. According to this example, the slave device may include a power supply and circuitry capable of responding to communicated information from the ICD wherein the responding includes delivery of electroacupuncture therapy by the slave device. Alternatively, a slave device may notify a patient to administer acupuncture or related therapy.

In a third scenario 430, an ICD includes a frequency or pulse generator that controls stimulation frequency of a slave device (e.g., an electroacupuncture, TENS, etc.). For example, the ICD may select a stimulation frequency of approximately 1 Hz to approximately 5 Hz or higher depending on need. In this example, the slave device stimulator has a power supply and circuitry capable of responding to the control frequency signal from the ICD. Accordingly, the slave device only needs to respond to the frequency or pulse generator of the ICD. In this example, the slave device depends on the ICD to a greater degree that the slave devices of the first scenario 410 and the second scenario 420.

In a fourth scenario 440, an ICD operates as a pulse generator, power supply, etc., for a slave device. According to this exemplary scenario, the slave device includes one or more electrodes that discharge power supplied by the ICD. For example, an ICD may supply power to a slave device via a lead. Thus, according to this scenario, the slave device is highly dependent on the ICD. This scenario includes ICDs having electrode-bearing leads suitable for stimulation at or near acupoints.

Figure 5:
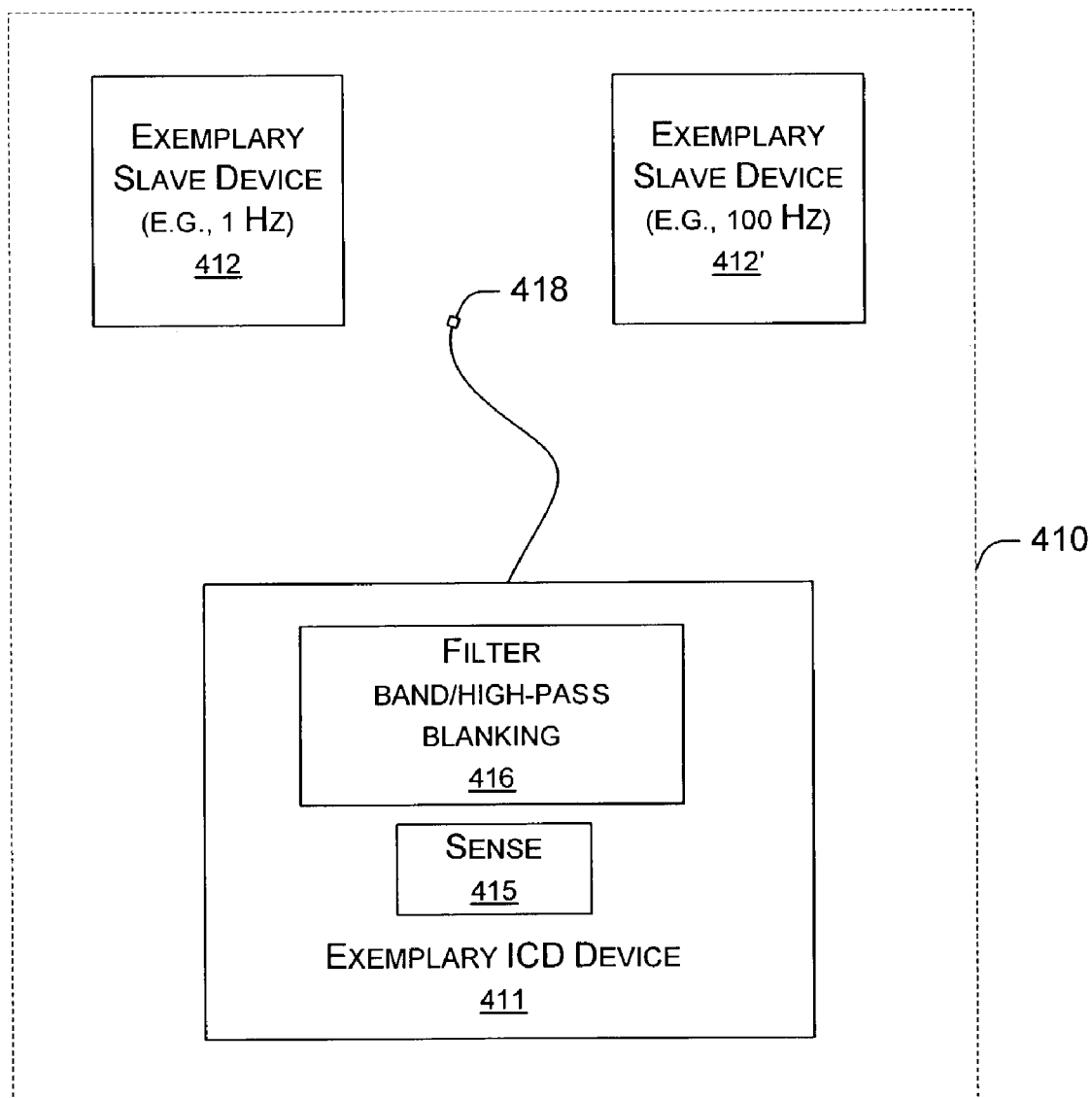
FIG. 5 is a block diagram of an exemplary implantable cardiac device (ICD) and two exemplary slave devices capable of operation according to the scenario 410 of FIG. 4.

Referring to FIG. 5, an exemplary ICD 411 capable of operation according to the scenario 410 of FIG. 4 is shown. This particular example includes a first slave device 412 capable of delivering stimuli at approximately 1 Hz and a second slave device 412' capable of delivering stimuli at approximately 100 Hz. The ICD 411 includes a sense module 415, a filter module 416 and a sense lead 418 having one or more electrodes. The filter module 416 ensures that electromagnetic interference generated by either slave device 412, 412' does not interfere with operation of the sense module 415. The filter module 416 optionally includes a multi-pole bandpass filter wherein a bandpass frequency range of approximately 20 to approximately 40 Hz may optimally allow for passage of R-waves while blocking frequencies associated with the two (e.g., 1 Hz and 100 Hz) electroaccupuncture signals. Further, the ICD 411 optionally includes circuitry to detect a stimulation session and to respond to such detection, for example, by switching on appropriate ICD features (e.g., filtering, blanking, cessation of operation, etc.).

Figure 6:
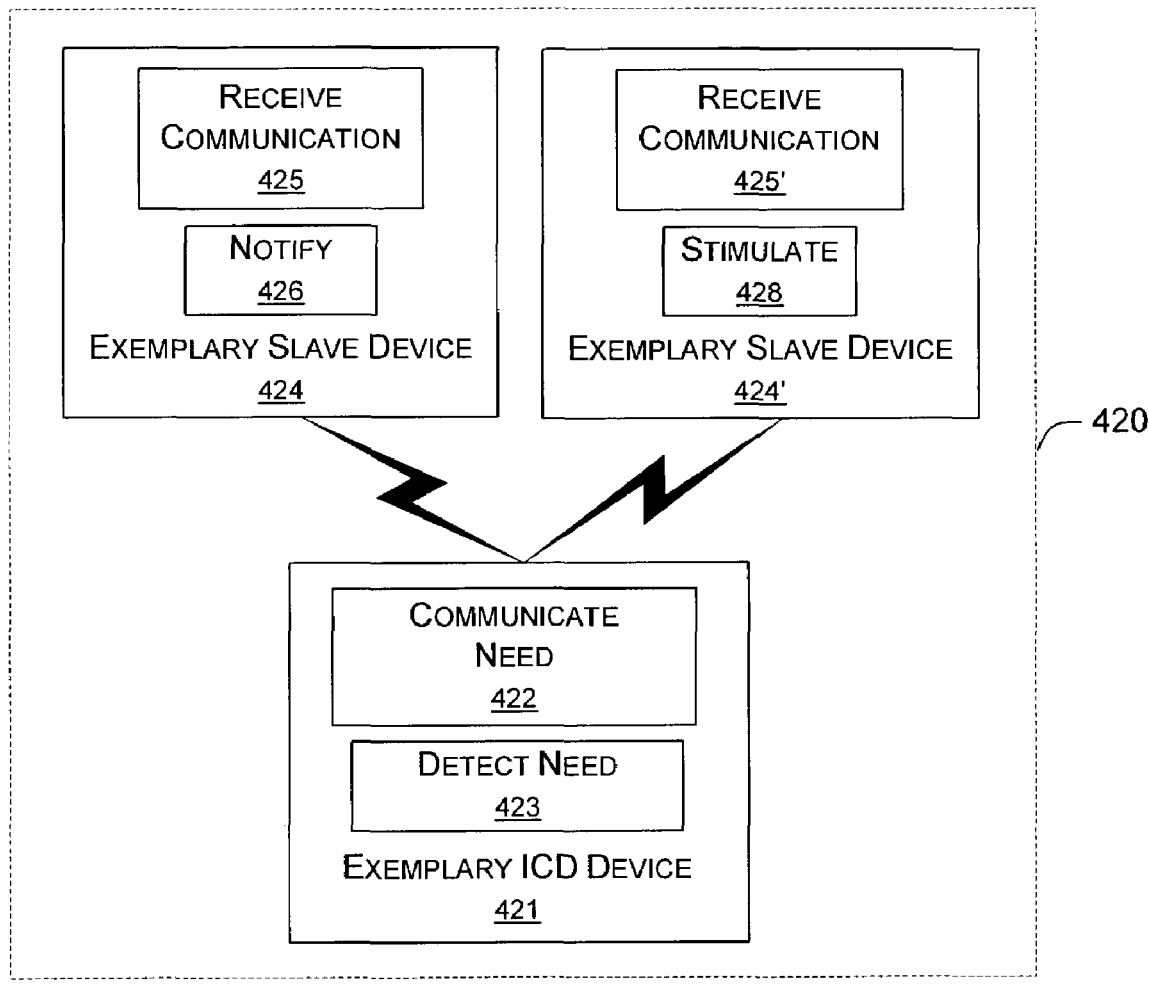
FIG. 6 is a block diagram of an exemplary implantable cardiac device (ICD) and two exemplary slave devices capable of operation according to the scenario 420 of FIG. 4.

Referring to FIG. 6, an exemplary ICD 421 capable of operation according to the scenario 420 of FIG. 4 is shown. This particular example includes a first slave device 424 capable of notifying and a second slave device 424' capable of delivering stimuli. The slave device 424 includes a communication module 425 for receiving communications and a notification module 426 for notifying a patient or another individual (e.g., via another link, network, etc.). The slave device 424' includes a communication module 425' for receiving communications and a stimulation module 428 for stimulating an acupoint. The ICD 421 includes a communications module 422 for communicating a need and a detection module 423 for detecting a need for acupoint stimulation. The ICD 421 optionally includes features of the ICD 411 of FIG. 5 (e.g., filtering, blanking, bandpass filter, etc.).

Figure 7:
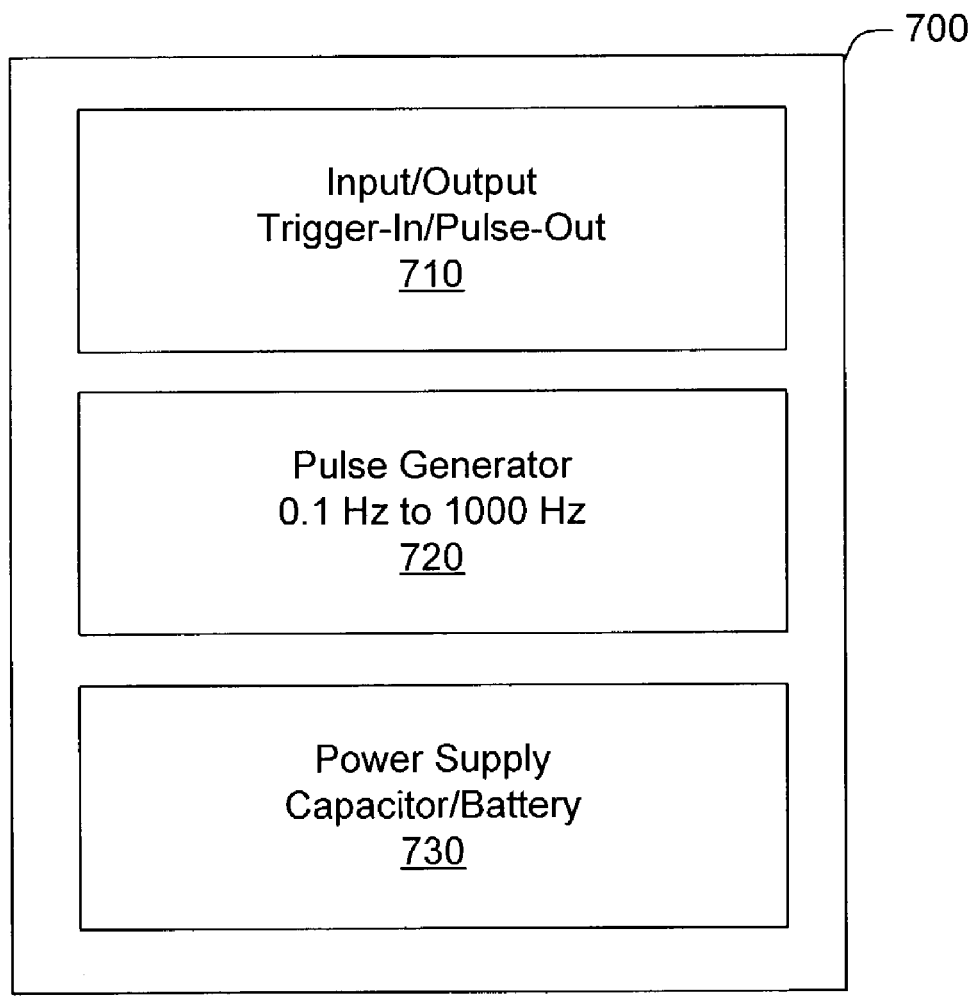
FIG. 7 is a block diagram of an exemplary slave device.

FIG. 7 shows an exemplary slave device 700. The exemplary slave device 700 includes an input/output or communications module 710, a pulse generator module 720 and a power supply module 730. This particular slave device 700 optionally operates according to the exemplary scenario 420 of FIG. 4. For example, the input/output module 710 has circuitry for receiving and/or responding to a signal communicated from an ICD (e.g., an electromagnetic signal). Such a signal optionally includes information regarding frequency of stimulation (e.g., acupoint stimulation), power of stimulation and/or duration of stimulation.

Figure 8:
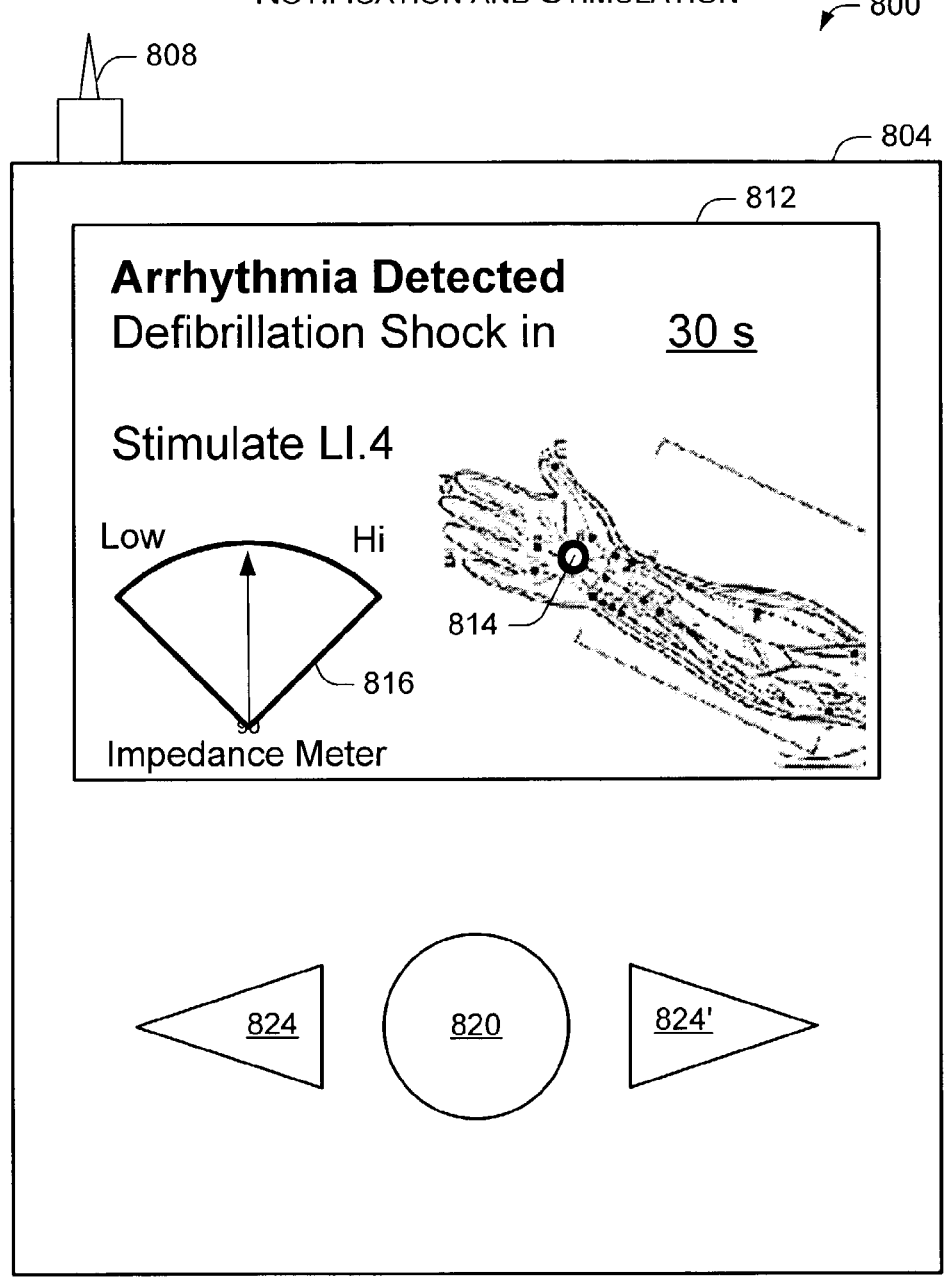
FIG. 8 is a diagram of an exemplary slave device that includes a display.

FIG. 8 shows an exemplary slave device 800 for notification and stimulation of an acupoint. The slave device 800 includes a case 804, a stimulation electrode 808 (or electrodes), a display 812 and operational buttons 820, 824, 824'. When such a device is used to stimulate an acupoint on a patient, the case 804 may function as an electrode when in contact with the patient's body (e.g., when held in the patient's hand, etc.). For example, the electrode 808 may be positioned at or near an acupoint and the case 804 may act as a return electrode.

The display 812 includes a variety of textual and/or graphical information germane to operation. For example, the display may display text indicating a cardiac condition (e.g., "arrhythmia detected") and a course of action to be taken by an implanted cardiac device (e.g., "defibrillation shock in 30 s"). Further, the display may display text to indicate a course of action to be taken by a patient (e.g., "stimulate LI.4"). Yet further, the display may display a graphical representation of the location of one or more acupoints and may even highlight a particular acupoint (see, e.g., acupoint 814).

The exemplary slave device 800 also includes an impedance meter having a graphical display 816. Accordingly, a patient positions the electrode 808 using impedance measurements as a guide to indicate proper positioning of the electrode 808 with respect to an acupoint. Various studies have shown that skin impedance changes at or near an acupoint. Thus, the impedance feature of the exemplary device 800 may aid in positioning of the stimulation electrode 808. An impedance circuit of the slave device 800 may aid in the positioning of an electrode for electroacupuncture therapy. Further, such a circuit may be used to locate a point having a known impedance, for example, a patient may measure and record impedance for an acupoint or other point using the circuit and/or another circuit and then use the measured and recorded impedance to relocate the acupoint or other point.

The exemplary slave device 800 has one or more operation buttons 820, 824, 824', which may aid a user in positioning the electrode 808, understanding cardiac condition, and/or delivering a stimulus at or near an acupoint. Alternatively, a slave device may include a touch-sensitive display that allows for user operation.

An exemplary method of use for the slave device 800 may commence after an ICD detects an arrhythmia. For example, the ICD may detect an arrhythmia, determine that a defibrillation shock is desirable and then communicate related information to the slave device 800. The slave device 800 may then display information such as "arrhythmia detected" and "defibrillation shock in X seconds", where X may be a timer that counts down the number of seconds until delivery of a defibrillation shock by the ICD. Alternatively, the slave device 800 may have control over delivery of the defibrillation shock whereby a user presses the button 820, which, in turn, causes the slave device to communicate with the ICD and call for delivery of the defibrillation shock. In either instance, the user is given time to deliver acupoint stimulation prior to the delivery of the defibrillation shock.

Regarding the displayed information, such information can help a user to locate an acupoint quickly. For example, the ICD and/or the slave device may direct a user to stimulate a particular acupoint based on a cardiac condition detected by the ICD. The slave device may then display a graphic showing the location of the acupoint. Further, the user may use an impedance measurement if available. Once the user has adequately positioned the electrode, then acupoint stimulation may occur.

Alternatively, the stimulation electrode may be supplied with power immediately after communication of a need from the ICD. In this instance, the user need only position the electrode at or near the acupoint to initiate acupuncture therapy.

Another exemplary slave device for notification and/or stimulation has a band to secure the device on a patient's limb. Further, such a device optionally includes one or more electrodes in electrical contact with the patient's skin at or near an acupoint. For example, an exemplary slave device optionally resembles a wrist-watch wherein the underside of the device has one or more electrodes positionable at or near an acupoint. Such a slave device may operate based on information communicated by an ICD. Of course, a variety of other slave device configurations are possible.

Regarding communicated information from an ICD, such an implanted device may communicate a code to the exemplary slave device 800. The slave device 800 may include a lookup table or other database wherein the code is used to determine one or more parameters germane to acupoint stimulation. An exemplary table, Table 1, appears below.

TABLE 1

Exemplary Code Lookup Table

| Code | Acupoint | Power | Frequency | Duration |
|---|---|---|---|---|
| 001 | 4 | 1 | 5 | 10 |
| 010 | 15 | 3 | 2 | 5 |
| 011 | 6, 8 | 2, 2 | 1, 5 | 20, 5 |
| 100 | 4 | 9 | 8 | 8 |

According to the exemplary Table 1, a code (e.g., a binary code) is communicated from the implantable device to the slave device. The slave device then correlates the code with one or more acupoints and acupoint stimulation parameters. Note that the code "001" and the code "100" correspond to the same acupoint, however, the acupoint stimulation parameters differ. For example, as described herein, different stimulation parameters (power, frequency, duration, etc.) may produce different effects. The exemplary Table 1, may be updated (e.g., manually, via a network link, etc.) based on patient, acupoint and/or other information (e.g., new studies, etc.). An exemplary method of using such a table or database may include software, firmware, and/or hardware to correlate a code with one or more acupoints, parameters, pieces of information, etc.

Exemplary Acupoints

As already mentioned, acupoints generally lie along various meridians. The twelve main meridians together with two vessel meridians are often referred to as "the fourteen meridians". The twelve main meridians are distributed symmetrically at the left and right sides of the body and include those associated with bladder (BL), gall bladder (GB), heart (HE), kidney (KI), large intestine (LI), liver (LV), lung (LU), pericardium (PE), small intestine (SI), spleen (SP), stomach (ST), and triple burner or warmer (TW). The two vessel meridians (Du or governing vessel (GV) [back midline] and Ren or conception vessel (CV) [front midline]) of the fourteen meridians emerge from the perineum, and ascend respectively along the midlines of the front and back of the body.

Acupuncture and Cardiac Function, Analgesia, Etc.

Traditional Chinese medicine has recognized acupuncture as a suitable therapy for treatment of cardiac function and/or related disorders. Jiang, "Clinical effects of acupuncture on cardiovascular diseases", (available at www.ucihs.uci.edu/com/samueli/conferences/abstracts/jiang.htm), reported that clinical effects of acupuncture on angina pectoris, myocardial infarction, arrhythmia, tachycardia, bradycardia, hypertension, hyperlipidemia, viral myocarditis, rheumatic heart disease, chronic pulmonary heart disease, and heart arrest have been significant. Jiang noted that acupuncture can improve oxygen supply to the heart muscle and promote recovery of ischemic myocardium as well as a decrease in low frequency cardiac autonomic nerve activity (e.g., 0.04-0.15 Hz) and an increase high frequency cardiac autonomic nerve activity (e.g., 0.15-0.40 Hz), which are potentially useful as indicators of cardiac vagal activity and sympathovagal balance. Jiang reported that the acupoint PE.6 was a main point for effecting cardiac function while stimulation at the acupoints "Huatuo Jiaji", BL.15, CV.17, BL.14, CV.6, SP.6, and ST.36 was also useful. Other useful acupoints include, but are not limited to, CV.9, CV.12, CV.14, CV.17, GV.9, PE.4, PE.5, LU.5, and ST.40.

Various studies have reported depressor and/or pressor effects produced by acupoint stimulation. For example, Wu, et al., reported substantial bradycardia by manual acupuncture at LI.4 (left hand) and ST.36 (left leg). At ST.36 and LI.11, Li, "Factors influence the effect of acupuncture on cardiovascular system", (available at www.ucihs.uci.edu/com/samueli/conferences/abstracts/li.htm), used electroacupuncture and reported a current dependent effect in that low current (e.g., 300 microamperes) produced a depressor response and that more current produced a pressor response (e.g., >600 microamperes). A study by Ku et al., "Tinggong (SI.19), a novel acupoint for 2 Hz electroacupuncture-induced depressor response," *Acupunct. Electrother. Res.*, 18(2):89-96 (1993), also reported a depressor response for 2 Hz (3 V) electroacupuncture at acupoint LI.11 and at SI.19; however, for stimulation at a frequency of 10 Hz a depressor response was not observed. A study by Yang et al., "Effect of electroacupuncutre on response to immobilization stress," *Pharmacol. Biochem. Behav.*, 72(4):847-855 (2002), reported that electroacupuncture (3 Hz, 0.2 ms pulses, 20 mA) at acupoint PE.6 or acupoint HE.3 reduced expected increases in blood pressure and heart rate and attenuated plasma levels of norepinephrine and epinephrine. A study by Nishijo, et al., "Decreased heart rate by acupuncture stimulation in humans via facilitation of cardiac vagal activity and suppression of cardiac sympathetic nerve," *Neurosci. Lett.*, 227(3):165-8 (1997), reported a depressor response due to stimulation at acupoint PE.6. More specifically, Nishijo et al. noted a decrease in heart rate and sympathetic activity and an increase in vagal tone. Stimulation of acupoint PE.6 has been known traditionally to alleviate chest and/or heart pain. A study by Li et al., "Reversal of reflex-induced myocardial ischemia by median nerve stimulation: a feline model of electroacupuncture," *Circulation;* 97:1186-1194 (1998), reported that low frequency (1 Hz to 5 Hz) stimulation of A-fibers or A- and C-fibers of the median nerve resulted in a depressor effect, whereas activation of C-fibers alone produces a pressor response. Li et al., further noted that similar results were known for stimulation at the acupoint PE.6, which helps to provide a physiological basis for the reported efficacy of acupuncture in the treatment of angina pectoris.

Various studies have reported pressor responses, for example, Lee et al., "Some effects of acupuncture at Jen chung (Go-26) [Renzhong, GV.26] on cardiovascular dynamics in dogs," *Can. J. Comp. Med.* 41:446-454 (1977) used moxibuston by electrocautery and needling with twirling at acupoint GV.26 to produce a significant increase in heart rate and mean arterial pressure. Numerous studies reported a pressor response for stimulation at PE.6. For example, Syuu et al., "Cardiovascular beneficial effects of electroacupuncture at Neiguan (PC-6) [PE.6] acupoint in anesthetized open-chest dog," *Jpn. J. Physiol.*, 51(2):231-8 (2001), reported that electroacupuncture at 40 Hz produced an increase in end-systolic elastance, arterial pressure, end-diastolic volume, heart rate, stroke volume, cardiac output, and end-systolic pressure. Again, Li, supra, noted a current dependent effect at PE.6; thus, depending on stimulation conditions, some studies may show a pressor response at PE.6 while others may show a depressor response. Li, supra, also reported that stimulation at either acupoint LI.6 or acupoint GB.39 resulted in a pressor response.

Exemplary Method of Acupoint PE.6 Stimulation—Cardiac Function

In humans, the acupoint PE.6 is located on in the middle of the forearm (palm side) between the tendons and approximately 3 fingerbreadths above the wrist crease. Stimulation at the acupoint PE.6 has been known traditionally to aid in nourishing the heart, calming the spirit, and promoting smooth circulation of Qi and blood. Stimulation at the acupoint PE.6 has been used, for example, to treat angina (Zhou et al., "Metrological analysis for efficacy of acupuncture on angina pectoris," *Zhongguo Zhong Xi Yi Jie He Za Zhi*, 13(4):212-214 (1993)), improve sin-atrial conduction (Xi, et al., "Effect of electro-acupuncture at Neiguan P6 on sin-atrial conduction in patients without sick sinus syndrome," *Zhongquo Zhong Xi Yi Jie He Za Zhi*, 13(11):663-664, 644 (1993)), prevent and cure arrhythmia (Huang, "Effect of electroacupuncture at Neiguan point on transmembrane potential of the ventricular cells of rabbits with acute myocardial ischemia in situ," *Zhen Ci Yan Jiu*, 20(2):33-35 (1995)), diminish heart rate variability (Shi et al., "Effect of acupuncture on heart rate variability in coronary heart disease patients," *Zhongguo Zhong Xi Yi Jie He Za Zhi*, 15(9):536-538 (1995)), and decrease heart rate (Lin, "Effect of acupuncture on cardiopulmonary function," *Chin. Med. J.*, 109(6):482-485 (1996)).

An exemplary method involves stimulation the acupoint PE.6, for example, to treat aforementioned conditions and/or to produce aforementioned results. Such acupoint stimulation may directly or indirectly modulate hypothalamic activity, amygdalic activity, activity of the raphe/parapyrimidal region and/or activity of the rostral ventrolateral medulla (rVLM). For example, electroacupuncture at PE.6 has been shown to invoke use of an opioid-related mechanism in the rVLM to inhibit sympathetic-induced increases in blood pressure (e.g., Li et al., "Rostral ventrolateral medullary opioid receptor subtypes in the inhibitory effect of electroacupuncture on reflex autonomic response in cats," *Auton. Neurosci.*, 89(1-2):38-47 (2001)). Further, the amygdala is known to have an important role in controlling cardiovascular functions (e.g., Baklavadzhyan, et al., "Studies of the role of the central nucleus of the amygdala in controlling cardiovascular functions," *Neurosci. Behav. Physiol.* 30(20):231-236 (2000)). Yet further, stimulation at the acupoint PE.6 has been reported to affect amygdala activity (e.g., Lai et al., "Role of amygdaloid nucleus in the correlation between the heart and the acupoint Neiguan in rabbits," *J. Tradit. Chin. Med.*, 11(2):128-38 (1991)). Another study by Ku, et al., "Beta-endorphin- and GABA-mediated depressor effect of specific electroacupuncture surpasses pressor response of emotional circuit," *Peptides*, 22(9):1465-70 (2001), reported that electroacupuncture can activate beta-endorphin(beta-EP)ergic and noradrenergic neurons projecting to the rVLM wherein the latter acts upon the rVLM-GABAergic interneurons to thereby produce a depressor effect. Ku, et al., also reported that the depressor effect is strong enough to surpass the pressor response of the nucleus amygdaloideus centralis (AC) and that both beta-endorphin (beta-EP) and GABA in the rVLM mediate the electroacupuncture (EA) antagonistic effect. Ku, et al., added that "the EA effect does not take place in the AC and paraventricular nucleus"; however, Hui, et al., "Acupuncture modulates the limbic system and subcortical gray structures of the human brain: evidence from fMRI studies in normal subjects," *Hum. Brain Mapp.*, 9(1):13-25 (2000), reported that stimulation at the acupoint LI.4 lead to prominent decreases in fMRI signals (e.g., decreased activity) of the nucleus accumbens, amygdala, hippocampus, parahippocampus, hypothalamus, ventral tegmental area, anterior cingulate gyrus (BA 24), caudate, putamen, temporal pole, and insula. Therefore, a direct or indirect effect on such brain regions is apparent for at least some acupoints. Indeed, decreased activity of the amygdala is associated with a depressor response while increased activity of the amygdala is associated with a pressor response (e.g., Nalivaiko et al., "Raphe region mediates changes in cutaneous vascular tone elicited by stimulation of amygdala and hypothalamus in rabbits," *Brain Res.*, 891(1-2):130-137 (2001)). According to Nalivaiko et al., administration of muscimol toxin to the rVLM strongly attenuated hypothalamic induced mesenteric vasoconstriction whereas administration of muscimol to the raphe/parapyramidal region eliminated amygdalic and hypothalamic induced skin vasoconstriction. In general, stimulation at the acupoint PE.6 can also counteract such sympathetic responses.

Some studies indicate that stimulation of the acupoint PE.6 results in stimulation of underlying nerves, particularly group III and IV somatic afferents. Chao et al., "Naloxone reverses inhibitory effect of electroacupuncture on sympathetic cardiovascular reflex responses," *Heart Circ. Physiol.*, 276(6): H2127-H2134 (1999), reported that stimulation of the acupoint PE.6 and direct stimulation of the median nerves underlying the acupoint PE.6 produced similar effects and postulated that stimulation of the median nerve serves as a trigger event. Thus, according to an exemplary method, stimulation of the acupoint PE.6 includes stimulation of an underlying median nerve. Chao, et al., further noted that the PE.6 or median nerve depressor response may occur via inhibition of sympathetic neurons in the nucleus paragigantocellularis lateralis (PGL) of the rVLM.

Figure 9:
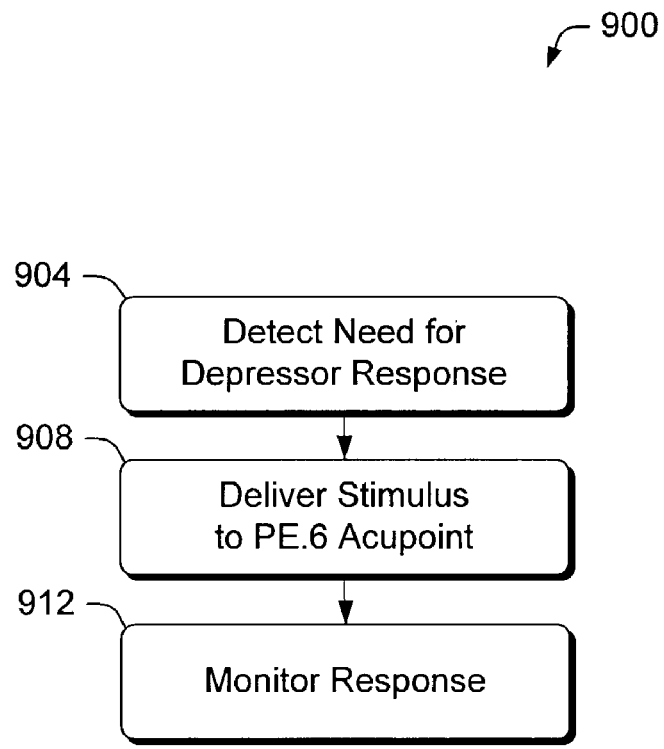
FIG. 9 is a block diagram of an exemplary method for delivering power to the acupoint PE.6.

Referring to FIG. 9, an exemplary method 900 for stimulating the acupoint PE.6 is shown. In a detection block 904, an ICD detects a need for a depressor response. For example, the exemplary ICD 100 of FIG. 1 uses various sensing and detection capabilities that indicate a need for decreased blood pressure. Responsive to detection of the need, a delivery block 908 delivers power (e.g., a stimulus or stimuli) to the acupoint PE.6 to thereby elicit a depressor response. The delivery of power in the delivery block 908 may occur via any suitable device, including the slave devices of the exemplary scenarios of FIG. 4. Alternatively, acupuncture therapy occurs via any suitable technique after a notification block which notifies a patient of the need for a depressor response. A monitor block 912 follows wherein the ICD monitors physiologic response to the delivery. The delivery optionally continues until an appropriate physiologic response occurs or for a specified duration, which may be repeated one or more times in an effort to achieve a desirable physiologic response.

In another exemplary method, a detection block detects a need for a pressor response. Upon detection of such a need, a delivery block delivers power (e.g., a stimulus or stimuli) in an effort to cause a pressor response. As noted above, several studies indicate that higher current levels may cause stimulation at the acupoint PE.6 to produce a pressor response. Further, stimulation frequency (frequency of delivered power) is optionally adjusted in an effort to produce a pressor response, as opposed to a depressor response.

Exemplary Method of Acupoint LI.4 Stimulation—Analgesia

The acupoint LI.4 is located on the dorsum of the hand, between the 1st and 2nd metacarpal bones, approximately in the middle of the 2nd metacarpal bone on the radial side. Traditional indications include, for example, general pain, headache, neck pain, redness, eye swelling and pain, toothache, sore throat, facial paralysis, abdominal pain, dysentery, constipation, amenorrhea, delayed labor, and infantile convulsion. As mentioned above, Hui, et al., "Acupuncture modulates the limbic system and subcortical gray structures of the human brain: evidence from fMRI studies in normal subjects," *Hum. Brain Mapp.*, 9(1):13-25 (2000), reported that stimulation at the acupoint LI.4 lead to prominent decreases in fMRI signals (e.g., decreased activity) of the nucleus accumbens, amygdala, hippocampus, parahippocampus, hypothalamus, ventral tegmental area, anterior cingulate gyrus (BA 24), caudate, putamen, temporal pole, and insula. Hui, et al., also observed signal increases (e.g., increased activity) primarily in the somatosensory cortex. Thus, stimulation at the acupoint LI.4 produces a variety of effects.

Figure 10:
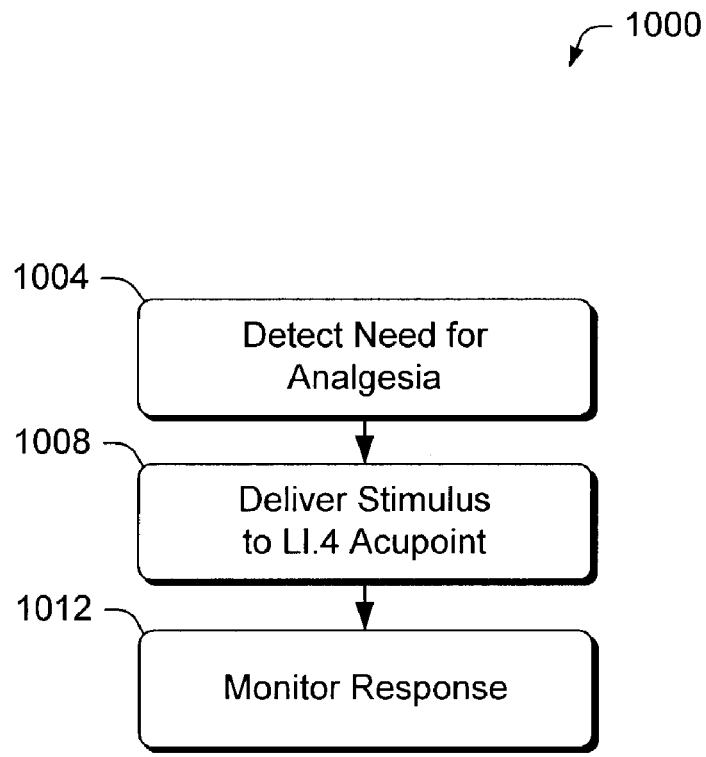
FIG. 10 is a block diagram of an exemplary method for delivering power to the acupoint LI.4.

Referring to FIG. 10, an exemplary method 1000 for stimulating the acupoint LI.4 is shown. In a detection block 1004, an ICD detects a need for analgesia. For example, the exemplary ICD 100 of FIG. 1 uses various sensing, detection and/or other capabilities to detect a need for analgesia. A detected need for analgesia may be due to a patient experiencing pain (e.g., angina, etc.) and/or because of an impending cardioversion or defibrillation stimulus or stimuli (e.g., including shock). Responsive to detection of the need, a delivery block 1008 delivers power (e.g., a stimulus or stimuli) to the acupoint LI.4 to thereby elicit an analgesic response. The delivery of power in the delivery block 1008 may occur via any suitable device, including the slave devices of the exemplary scenarios of FIG. 4. Alternatively, acupuncture therapy occurs via any suitable technique after a notification block which notifies a patient of the need for analgesia. A monitor block 1012 follows wherein the ICD monitors physiologic response to the delivery. The delivery optionally continues until an appropriate physiologic response occurs or for a specified duration, which may be repeated one or more times in an effort to achieve a desirable physiologic response.

A study by Wang et al., "Effect of the intensity of transcutaneous acupoint electrical stimulation on the post-operative analgesic requirement," *Anesth. Analg.*, 85(2): 406-13 (1997), reported that transcutaneous electrical stimulation at the acupoint LI.4 and at incision points (e.g., at 9 mA to 12 mA, alternating at 2 Hz and 100 Hz every 3 s, with stimulation at the acupoint and incision alternated every 6 s and every 2 h for 30 min while awake) produced a significant decrease in post-operative opioid requirement. Accordingly, the aforementioned exemplary method and/or other methods, optionally stimulate the acupoint LI.4 at approximately 2 Hz and/or approximately 100 Hz for a period of approximately 30 minutes in an effort to produce an analgesic effect.

Exemplary Method of Acupoint GV.26 Stimulation

The acupoint GV.26 is located along the midline at the junction of the upper and lower portions of the upper lip. Traditionally, indications for stimulation at the acupoint GV.26 include controlling seizures, cardiac arrest, and syncope. A review by Rogers et al., "Emergency acupoint Renzhong (Jenchung, GV26): a bibliography and review from textbook sources," *The Medical Acupuncture Web Page*, (http://users.med.auth.qr/~karanik/english/articles/gv26.htm) reported that stimulation at the acupoint GV.26 could enhance cardiovascular and cerebrovascular function. For example, stimulation at GV.26 was effective in cardioversion in atrial fibrillation, strengthened left ventricular function, inhibited experimental cardiac pain, increased the activity of SDH and LDH in myocardium and protected against damage to myocardial cells. Stimulation at GV.26 was also reported to have sympathomimetic effects on cardiovascular systems in animals under halothane anaesthesia; pressor effects in hemorrhagic shock and ischemic hypotension; and enhance brain perfusion (e.g., increased $P-O_2$ in the frontal cortex, decreased peripheral arterial resistance, relaxed spasm, increased blood flow in the carotid and cerebral arteries and hastened clinical recovery after cerebrovascular accidents). A study by Chen, "Acupuncture and herbs in the treatment of neurodegenerative disorders: Alzheimer's disease, stroke, and Parkinson's disease," *Med. Acupuncture*, 11(1), (1999), reported that the combination of stimulation at the acupoints PE.6 and GV.26 has been found to increase the contractile strength of the heart and the cardiac output of blood circulation to the brain. A study by Chen et al., "Role of rostral ventrolateral medulla in the 'renzhong' [GV.26] induced pressor response in rabbits," *Hua Xi Yi Ke Da Xue Xue Bao*, 22(4):387-90 (1991), reported that stimulation of the acupoint GV.26 increased arterial blood pressure and affected the rVLM while administration of a toxin to the rVLM abolished the GV.26 acupoint's pressor effect. Thus, as with stimulation at other acupoints, some degree of brain activation/deactivation is involved with stimulation at the acupoint GV.26.

Figure 11:
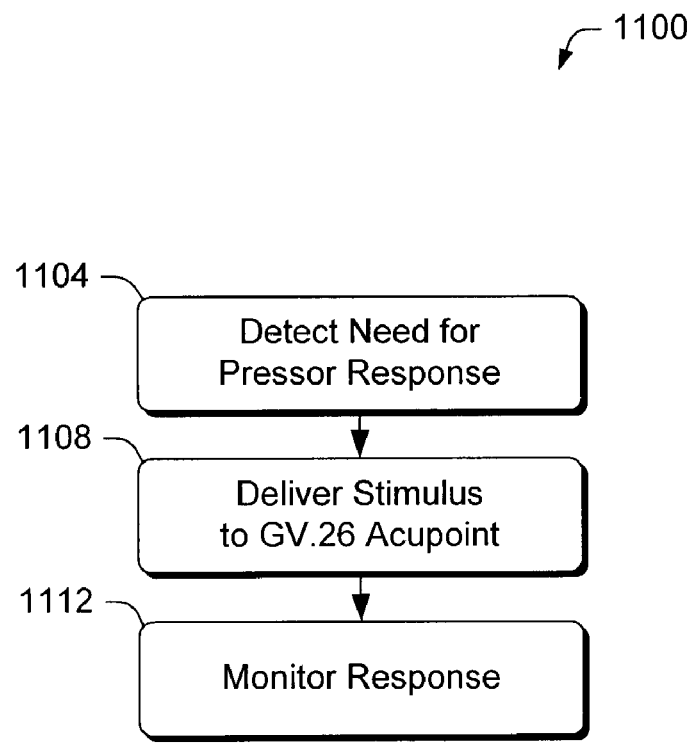
FIG. 11 is a block diagram of an exemplary method for delivering power to the acupoint GV.26.

Referring to FIG. 11, an exemplary method 1100 for stimulating the acupoint GV.26 is shown. In a detection block 1104, an ICD detects a need for a pressor response. For example, the exemplary ICD 100 of FIG. 1 uses various sensing and detection capabilities that indicate a need for an increase in blood pressure. Responsive to detection of the need, a delivery block 1108 delivers power (e.g., a stimulus or stimuli) to the acupoint GV.26 to thereby elicit a pressor response. The delivery of power in the delivery block 1108 may occur via any suitable device, including the slave devices of the exemplary scenarios of FIG. 4. Alternatively, acupuncture therapy occurs via any suitable technique after a notification block which notifies a patient of the need for a pressor response. A monitor block 1112 follows wherein the ICD monitors physiologic response to the delivery. The delivery optionally continues until an appropriate physiologic response occurs or for a specified duration, which may be repeated one or more times in an effort to achieve a desirable physiologic response.

Another exemplary method stimulates the acupoint PE.6 and the acupoint GV.26 to produce a pressor response. According to this particular example, stimulation parameters (e.g., power delivery parameters) for stimulation of the acupoint PE.6 are adjusted to produce a pressor response as opposed to a depressor response. Alternatively, depressor response stimulation parameters for acupoint PE.6 may be used to achieve a desirable physiologic response.

Exemplary Method of Acupoint GV.9 Stimulation

The acupoint GV.9 is located along the midline of the back, in the depression below the spinous process of the seventh thoracic vertebra. Traditional indications for stimulation the acupoint GV.9 include chest pain and chest tightness.

GV.9 (Zhiyang), see Yan et al., "Angiographic observation of immediate effect of electric pulse stimulation at Zhiyang point on coronary artery", *Zhongguo Zhong Xi Yi He Za Zhi*, 18(6):330-332 (1998). Stimulation at GV.9 produced an immediate and mild dilation of coronary arteries including left main coronary artery, left anterior descending artery, left circumflex coronary artery, and right coronary artery. 125 Hz and positive pulse width of 0.8 ms and negative pulse width of 0.4 ms, output voltage was 9 V.

Figure 12:
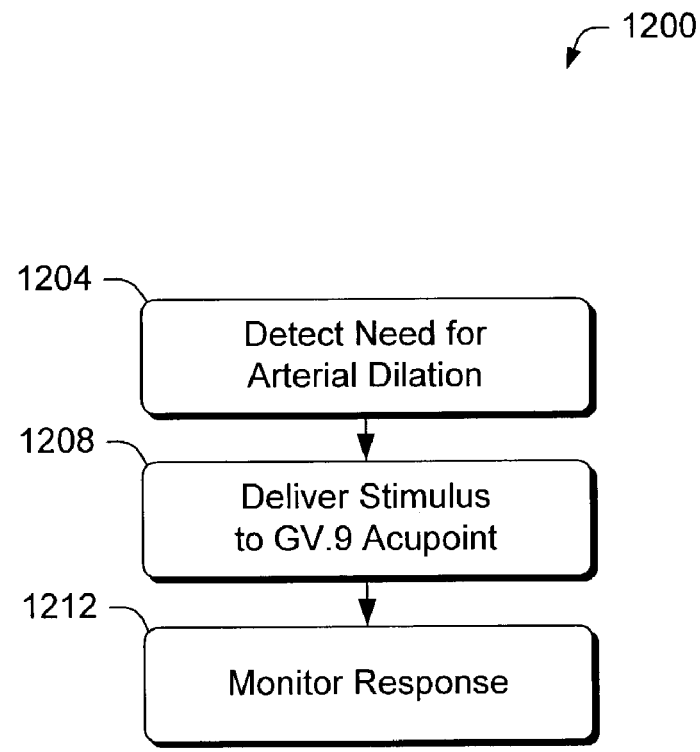
FIG. 12 is a block diagram of an exemplary method for delivering power to the acupoint GV.9.

Referring to FIG. 12, an exemplary method 1200 for stimulating the acupoint GV.9 is shown. In a detection block 1204, an ICD detects a need for arterial dilation. For example, the exemplary ICD 100 of FIG. 1 uses various sensing and detection capabilities that indicate a need for arterial dilation. Responsive to detection of the need, a delivery block 1208 delivers power (e.g., a stimulus or stimuli) to the acupoint GV.9 to thereby elicit arterial dilation. The delivery of power in the delivery block 1208 may occur via any suitable device, including the slave devices of the exemplary scenarios of FIG. 4. Alternatively, acupuncture therapy occurs via any suitable technique after a notification block which notifies a patient of the need for arterial dilation. A monitor block 1212 follows wherein the ICD monitors physiologic response to the delivery. The delivery optionally continues until an appropriate physiologic response occurs or for a specified duration, which may be repeated one or more times in an effort to achieve a desirable physiologic response.

Exemplary Methods of Stimulation of Heart Meridian

An exemplary method delivers a stimulus or stimuli to one or more points located along the heart meridian. The heart meridian includes nine acupoints. Descending along the arm are the acupoints HE.1 through HE.9. The acupoint HE.1 is located in the depression of the axilla; the acupoint HE.3 is located the medial end of the transverse cubital crease where the elbow is fully flexed; the acupoint HE.5 (Tongli) is located on the radial side of the tendon of flexor carpi ulnaris (heart rhythm); the acupoint HE.7 is located at the wrist joint, on the radial side of flexor carpi lunaris, in the depression at the proximal border of the pisiform bone; and the acupoint HE.9 is located on the dorsal aspect of the little finger, at the junction of lines drawn along the radial border of the nail and the base of the nail.

Exemplary Method for Minimizing Pain Associated with Shock

Figure 13:
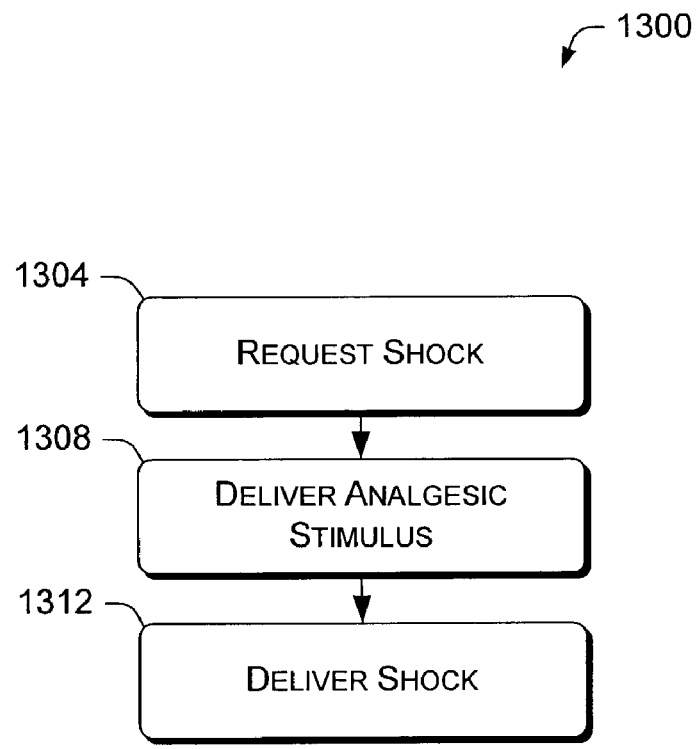
FIG. 13 is a block diagram of an exemplary method for delivering power to an acupoint for analgesia to minimize pain associated with a myocardial shock.

Referring to FIG. 13, an exemplary method 1300 for minimizing pain associated with shock is shown. In a request block 1304, an ICD requests a shock to the myocardium. A delivery block 1308 follows wherein power (e.g., a stimulus or stimuli) is delivered to one or more acupoints or points along a meridian in an effort to produce an analgesic effect. The delivery of power in the delivery block 1308 may occur via any suitable device, including the slave devices of the exemplary scenarios of FIG. 4. Alternatively, acupuncture therapy occurs via any suitable technique after a notification block which notifies a patient of an impending shock. Another delivery block 1312 then delivers the shock during and/or after the analgesic stimulation.

Figure 14:
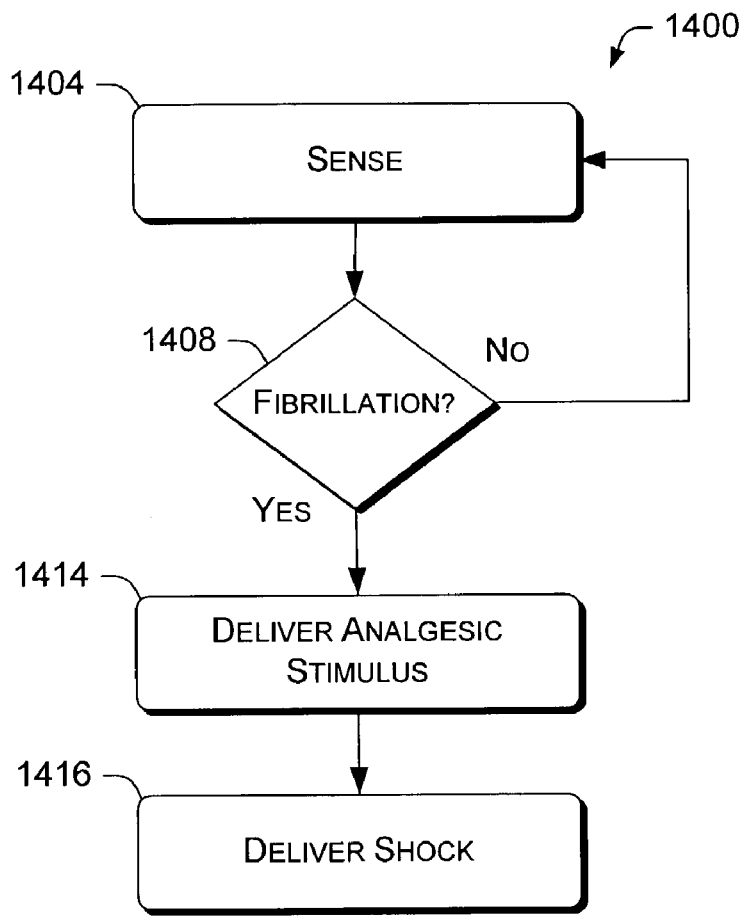
FIG. 14 is a block diagram of an exemplary method for delivering power to an acupoint for analgesia to minimize pain associated with defibrillation.

Referring to FIG. 14, another exemplary method 1400 for minimizing pain associated with shock is shown. In a sense block 1404, an ICD senses information germane to detection of fibrillation. For example, the exemplary ICD 100 of FIG. 1 has capabilities suitable for detection of atrial and/or ventricular fibrillation. A decision block 1408 follows wherein the ICD determines, on the basis of the sensed information and/or other information, whether fibrillation is indicated. If the decision block 1408 determines that fibrillation is not indicated, then the method 1400 continues at the sense block 1404. However, if the decision block 1208 determines that fibrillation is indicated, then a delivery block 1412 follows wherein power is delivered (e.g., one or more stimuli) to one or more acupoints and/or points along a meridian in an effort to produce an analgesic effect. The delivery of power in the delivery block 1412 may occur via any suitable device, including the slave devices of the exemplary scenarios of FIG. 4. Alternatively, acupuncture therapy occurs via any suitable technique after a notification block which notifies a patient of the particular cardiac condition and/or intended therapy. Following and/or during the delivery, another delivery block 1416 delivers a shock in an effort to defibrillate the myocardium (e.g., terminate the fibrillation).

Various exemplary methods associated with shock therapy are particularly suited to shock therapy for atrial conditions. Atrial shock therapy is optionally under patient control and thus typically allows for more than ample time for delivery of acupuncture therapy prior to shock therapy. Of course, various exemplary methods may also be used in conjunction with ventricular shock therapies.

Yet another exemplary method includes delivery of power at one or more acupoints that are known to produce an anti-arrhythmic effect. For example, Huang, supra, reported that stimulation at the acupoint PE.6 produced an anti-arrhythmic effect. For example, a delivery block may deliver power at the acupoint PE.6 in response to detection of an arrhythmia (e.g., fibrillation). Sensing may follow to determine if stimulation at the acupoint PE.6 successfully terminated the arrhythmia. In the case that stimulation at the acupoint PE.6 does not terminate the arrhythmia, then a shock may follow.

While various exemplary methods aim to cause an analgesic effect prior to therapy such as defibrillation shock, such methods are optionally used to cause an analgesic effect in instances where an implantable cardiac therapy device delivers in excess of approximately 100 mJ or greater than 1 mJ or 10 mJ above a pacing voltage. In general, acupoint stimulation may be beneficial anytime antiarrhythmia therapy would cause a patient to feel a sensation.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method comprising:
   using an implantable cardiac device to detect a cardiac condition having at least one of a corresponding electro therapy or a corresponding desired physiologic response;
   responsive to the detection, providing to an external device, information related to at least one of an acupoint therapy corresponding to the electro therapy or an acupoint therapy corresponding to the desired physiologic response, the information comprising acupoint location;
   using tissue impedance measurements to confirm the positioning of a stimulation device at or near the acupoint location; and
   responsive to the confirmation, delivering the acupoint therapy through the stimulation device.

2. The method of claim 1 wherein the desired physiologic response comprises a depressor response; and delivering energy comprises requesting delivery of power to the acupoint pericardium six (PE.6).

3. The method of claim 1 wherein the desired physiologic response comprises a pressor response; and delivering energy comprises requesting delivery of power to at least one of the acupoint pericardium six (PE.6) or the acupoint governing vessel twenty-six (GV.26).

4. The method of claim 1 wherein the electro therapy comprises a myocardial shock; and delivering energy comprises requesting delivery of power to the acupoint large intestine four (LI.4).

5. The method of claim 1 wherein the desired physiologic response comprises arterial dilation; and delivering energy comprises requesting delivery of power to the acupoint governing vessel nine (GV.9).

6. The method of claim 1 wherein the cardiac condition comprises an arrhythmia; and delivering energy comprises, requesting delivery of power to the acupoint pericardium six (PE.6).

7. The method of claim 1, wherein the acupoint comprises an acupoint along a meridian.

8. The method of claim 7, wherein the meridian comprises at least one of the heart meridian (HE), the pericardium meridian (PE) and the large intestine meridian (LI).

9. A system comprising:
   at least one electrode that is implantable within a patient and operative to sense cardiac activity and to generate corresponding signals;
   at least one acupoint stimulator positionable external the patient and operative to measure tissue impedance and stimulate an acupoint;
   a notification device; and
   circuitry in communication with the at least one electrode, the at least one acupoint stimulator, and the notification device and operative to:
     detect a cardiac event based on the signals from the at least one electrode, wherein the cardiac event has at least one of a corresponding electro therapy or a corresponding desired physiologic response;
     responsive to the cardiac event, provide to the notification device, information related to at least one of an acupoint therapy corresponding to the electro therapy or an acupoint therapy corresponding to the desired physiologic response, the information comprising acupoint location;
     use tissue impedance measurements to confirm the positioning of the at least one acupoint stimulator at the acupoint location; and
     responsive to the confirmation, control the acupoint stimulator to deliver acupoint therapy at the acupoint location.

10. The system of claim 9 wherein the acupoint stimulator comprises a slave device that is remotely controlled by the circuitry.

11. The system of claim 9 further comprising at least one lead configured for implantation within the patient, and wherein the at least one electrode is connected to the lead.

12. The system of claim 9 wherein the notification device is operative to present acupoint therapy information in a visually perceptible form.

13. The system of claim 9 wherein the acupoint stimulator comprises:
- at least one electrode for delivering the acupoint therapy; and
- tissue impedance measurement circuitry for aiding in the positioning of the electrode relative to the acupoint location.

* * * * *